US009462795B2

(12) United States Patent
Chin

(10) Patent No.: US 9,462,795 B2
(45) Date of Patent: Oct. 11, 2016

(54) APPARATUS FOR BREEDING FLY LARVAE

(76) Inventor: Byeong-Gyu Chin, Incheon (KR)

(*) Notice: Subject to any disclaimer, the term of this patent is extended or adjusted under 35 U.S.C. 154(b) by 125 days.

(21) Appl. No.: 14/358,348

(22) PCT Filed: May 11, 2012

(86) PCT No.: PCT/KR2012/003725
§ 371 (c)(1),
(2), (4) Date: May 15, 2014

(87) PCT Pub. No.: WO2013/151207
PCT Pub. Date: Oct. 10, 2013

(65) Prior Publication Data
US 2014/0261188 A1  Sep. 18, 2014

(30) Foreign Application Priority Data

Apr. 3, 2012 (KR) .................. 10-2012-0034562

(51) Int. Cl.
A01K 67/033 (2006.01)

(52) U.S. Cl.
CPC .................. A01K 67/033 (2013.01)

(58) Field of Classification Search
CPC .................. A01K 67/033; A01K 2227/706
USPC ......... 119/6.5, 6.6, 417, 418, 419, 420, 421, 119/455, 457
See application file for complete search history.

(56) References Cited

U.S. PATENT DOCUMENTS

| 1,974,549 | A | * | 9/1934 | Spencer | A01K 67/033 119/452 |
| 2,539,633 | A | * | 1/1951 | Morrill | A01K 67/033 119/6.5 |
| 4,036,177 | A | * | 7/1977 | DeSmit | A01K 31/005 119/457 |
| 4,411,220 | A | * | 10/1983 | Voegele | A01K 67/033 119/6.6 |
| 4,457,263 | A | * | 7/1984 | Cassou | A01K 31/10 119/455 |
| 4,765,274 | A | * | 8/1988 | Pizzol | A01K 67/033 119/6.6 |
| 8,499,719 | B2 | * | 8/2013 | Brocca | A01K 1/031 119/457 |
| 2008/0087231 | A1 | * | 4/2008 | Gabriel | A01K 1/031 119/455 |
| 2014/0020630 | A1 | * | 1/2014 | Courtright | A01K 29/00 119/6.6 |

FOREIGN PATENT DOCUMENTS

JP  09-172910 A  7/1997
JP  3134138 U  7/2007

(Continued)

Primary Examiner — Kristen C Hayes
Assistant Examiner — Ebony Evans
(74) Attorney, Agent, or Firm — Rabin & Berdo, P.C.

(57) ABSTRACT

The present invention relates to an apparatus for breeding fly larvae, and more particularly, to an apparatus for breeding fly larvae in which a breeding chamber is divided into multiple square sections to enable larvae to progressively grow and to complete the growth thereof, the larvae with the exception of those having escaped to an emergency chamber, are collected, and the larvae having escaped to the emergency chamber emerge as flies and are moved to a fly habitat chamber arranged above the breeding chamber to live and oviposit into the breeding chamber, and the above-described process is repeated so as to automatically breed larvae. To this end, the apparatus for breeding fly larvae of the present invention comprises: a fly habitat; a larvae-breeding area installed in the fly habitat; and a lid covering an upper portion of the larvae-breeding area, wherein the larvae-breeding area includes a pillar unit installed on the bottom of the fly habitat, and multiple breeding chambers installed in the pillar unit such that the breeding chambers operate independently.

10 Claims, 6 Drawing Sheets

(56) References Cited

FOREIGN PATENT DOCUMENTS

| KR | 20-0294434 | Y1 | 11/2002 |
| KR | 10-0654253 | B1 | 12/2006 |
| KR | 10-0731928 | B1 | 6/2007 |
| KR | 10-1044636 | B1 | 6/2011 |

* cited by examiner

APPARATUS FOR BREEDING FLY LARVAE

TECHNICAL FIELD

The present invention relates to an apparatus for consecutively breeding fly larvae, and in particular to an apparatus for consecutively breeding fly larvae which makes it possible to automatically breed larvae by repeatedly performing a process wherein in a state where a breeding chamber is divided into a plurality of breeding chambers configured to breed larvae in, the grownup larvae with the exception of those having escaped to a metamorphosis chamber are collected, and the larvae who escaped to the metamorphosis chamber are grown into flies, and the flies move to a habitat chamber installed above the breeding chambers and are bred and oviposit in the breeding chamber.

BACKGROUND ART

Generally speaking, fly larvae, more specifically, maggot are rich in protein, so they are usually used as feed or fishing bait.

According to a modern medical treatment, it is reported that maggot are inputted in a wounded portion where it is hard to conduct a surgical operation or where it is impossible to cure cleanly, for thereby curing rotten portions when the wound is severe or it is hard to distinguish dead skin from living skin.

There is not much provided the facility which is configured to enable a mass production of fly larvae which are being widely used in a variety of fields.

The Korean Patent Registration No. 10-0654253 describes "apparatus for breeding fly" configured so as to improve the above descried problems.

According to the Korean Patent Registration No. 10-0654253, a larvae breeding box is secured to a conveyor belt and is moved by one room per day, so the larvae may be bred under the controls of various breeding apparatuses which are fixed to the top and provide a proper habitat environment to each larvae growth stage.

However, the above-described related art has problems in that since the breeding box wherein larvae are grown is configured to drive, the amount of feed may increase due to the growth in terms of management, and it is hard to treat excretion, which results in decreased breeding efficiency.

As the fly larvae grow, their weights sharply increase, which needs to increase the capacity of facilities. The larvae may have big stress due to noise and vibrations during the operations of the fly breeding apparatus. Since the metamorphosis chamber is not directly connected, the grownup larvae should be manually selected and moved into the metamorphosis chamber, thus leading to bad work efficiency.

According to the above-described related art, in the related fly breeding apparatus, since the breeding box in which fly larvae inhabit is secured to the conveyer belt and is driven, the quality of breeding larvae is not much as compared with the facilities, and facility maintenance costs a lot. As a breeding facility designed to consecutively breed larvae in large quantity in a narrow space, the economic and feasibility and efficiency are bad.

In order to improve the above mentioned problems, the applicant of the present application has the Korean Patent Registration No. 10-1044636 of "apparatus for consecutively breeding larvae".

According to the Korean Patent Registration No. 10-1044636, seven independent breeding chambers are secured to one another in a circle, and various facilities are mounted on a cover which is identified as top of the breeding chambers. The consecutive breeding may be performed under a control management wherein feed are supplied at each growth stage as the cover rotates and forwardly moves stage by stage, and a habitat environment is maintained and controlled.

However, the Korean Patent Registration No. 10-1044636 has disadvantages in that since the breeding chambers are arranged in a circle, the area of the breeding chamber increases, and the management is hard and space application is bad.

DISCLOSURE OF INVENTION

Accordingly, the present invention is made in an effort to improve the above-described problems. It is an object of the present invention to provide an apparatus for breeding fly larvae which makes it possible to easily manufacture a larvae breeding part and to breed as many larvae as possible using the optimized spaces of the larvae breeding chambers in such a way that a plurality of independent breeding chambers in which larvae inhabit are made in a quadrangle shape and are configured to move along a rail stage by stage, and a cover of a breeding space on which many apparatuses are mounted is configured to vertically move in a fixed place and to cover top of the breeding space.

The larvae breeding chambers and the fly metamorphosis chamber are arranged in the bottom of a fly breeding part which is separated from the outside, thus providing optimized habitat environment. The larvae with the exception of those having escaped from the metamorphosis chamber after growth are collected, and the metamorphosed flies are moved to a fly habitat part and oviposit therein. The above-described process is repeatedly performed for thereby consecutively producing best larvae.

There are provided a plurality of breeding chambers formed in quadrangle shapes wherein larvae inhabit, and on the cover configured to cover the breeding chambers, various facilities configured to provide habitat environments proper to each growing stage are provided in place, and the quadrangle breeding chambers move under the cover which provide a growth environment by one room per day for thereby controlling the optimized habitat environment for larvae habitat. So, it is possible to prevent any load from being applied to the breeding apparatus of larvae, and the larvae may be bred economically and efficiently.

The breeding chambers are configured and arranged in quadrangle shapes such that the cover installed so as to provide the optimized breeding environment to larvae stage by stage and configured to cover tops of the plurality of the breeding chambers ascends as it is disengaged when the breeding chambers move, and the cover move forward to one side along the rail. The breeding chambers move under the cover which provides a predetermined habitat environment proper to the growth stages of larvae, and the cover descends and covers the bottoms of the breeding chambers. It is possible to economically breed the larvae, and the larvae can be automatically and consecutively bred, so mass production of larvae may be possible.

To achieve the above objects, there is provided an apparatus for consecutively breeding fly larvae, comprising a fly habitat part; a larvae breeding part which is installed in the fly habitat part; and a plurality of first through sixth covers which are configured to cover top of the larvae breeding part, wherein the larvae breeding part comprises a pillar unit which is installed on the floor of the fly habitat part; and a plurality of first to seventh breeding chambers which are installed in the pillar unit and are configured to independently operate with respect to one another.

Here, the pillar unit comprises a plurality of pillar members on top of which first through sixth covers are installed, and on top of the pillar member, an ascending and descending member is installed so as to ascend or descend the first through sixth covers, and in the center of the pillar member, a rail is installed so as to guide the first to seventh breeding chambers.

The pillar member comprises a locking member which is configured to fix the first through sixth covers.

The first to seventh breeding chambers are arranged in quadrangle shapes whose tops are open and have spaces inside them, and a passage is formed at one side of the first to seventh breeding chambers.

A wheel is installed in each corner of a lower side of each of the first to seventh breeding chambers and is mounted on the rail installed in the pillar member of the pillar unit.

A suction discharge unit configured to such and discharge impurities is installed at lower sides of the first to seventh breeding chambers.

Below the first to seventh breeding chambers, the suction discharge unit comprises a discharge container equipped with a filter inside, and a discharge pipe is installed at a lower side of the discharge container, and a vacuum pump is installed in the discharge pipe.

The first through sixth covers are separately installed while matching with the first to seventh breeding chambers, and any of the first to seventh breeding chambers is open.

A metamorphosis chamber is installed in the fly habitat chamber of the fly habitat part and is configured to communicate with the passage formed in the first to seventh breeding chambers of the larvae breeding part.

The metamorphosis chamber comprises a connection passage through which to communicate with the passage of the first to seventh breeding chambers, and an electronic scale sensor is installed at an end portion of the connection passage.

The breeding chambers are formed in quadrangle shapes.

The first to seventh breeding chambers move along the rail and move in a quadrangle closed loop.

Advantageous Effects

In the thusly configured present invention, it is possible to easily manufacture a larvae breeding part and to breed as many larvae as possible using the optimized spaces of the larvae breeding chambers in such a way that a plurality of independent breeding chambers in which larvae inhabit are made in a quadrangle shape and are configured to move along a rail stage by stage, and a cover of a breeding space on which many apparatuses are mounted is configured to vertically move in a fixed place and to cover top of the breeding space.

Also, the larvae breeding chambers and the fly metamorphosis chamber are arranged in the bottom of a fly breeding part which is separated from the outside, thus providing optimized habitat environment. The larvae with the exception of those having escaped from the metamorphosis chamber after growth are collected, and the metamorphosed flies are moved to a fly habitat part and oviposit therein. The above-described process is repeatedly performed for thereby consecutively producing best larvae.

Also, there are provided a plurality of breeding chambers formed in quadrangle shapes wherein larvae inhabit, and on the cover configured to cover the breeding chambers, various facilities configured to provide habitat environments proper to each growing stage are provided in place, and the quadrangle breeding chambers move under the cover which provide a growth environment by one room per day for thereby controlling the optimized habitat environment for larvae. So, it is possible to prevent any load from being applied to the breeding apparatus of larvae, and the larvae may be bred economically and efficiently.

In addition, the breeding chambers are configured and arranged in quadrangle shapes such that the cover installed so as to provide the optimized breeding environment to larvae stage by stage and configured to cover tops of the plurality of the breeding chambers ascends as it is disengaged when the breeding chambers move, and the cover move forward to one side along the rail. The breeding chambers move under the cover which provides a predetermined habitat environment proper to the growth stages of larvae, and the cover descends and covers the bottoms of the breeding chambers. It is possible to economically breed the larvae, and the larvae can be automatically and consecutively bred, so mass production of larvae may be possible.

BEST MODES FOR CARRYING OUT THE INVENTION

The apparatus for consecutively breeding fly larvae according to the present invention will be described with reference to the accompanying drawings.

Figure 1:
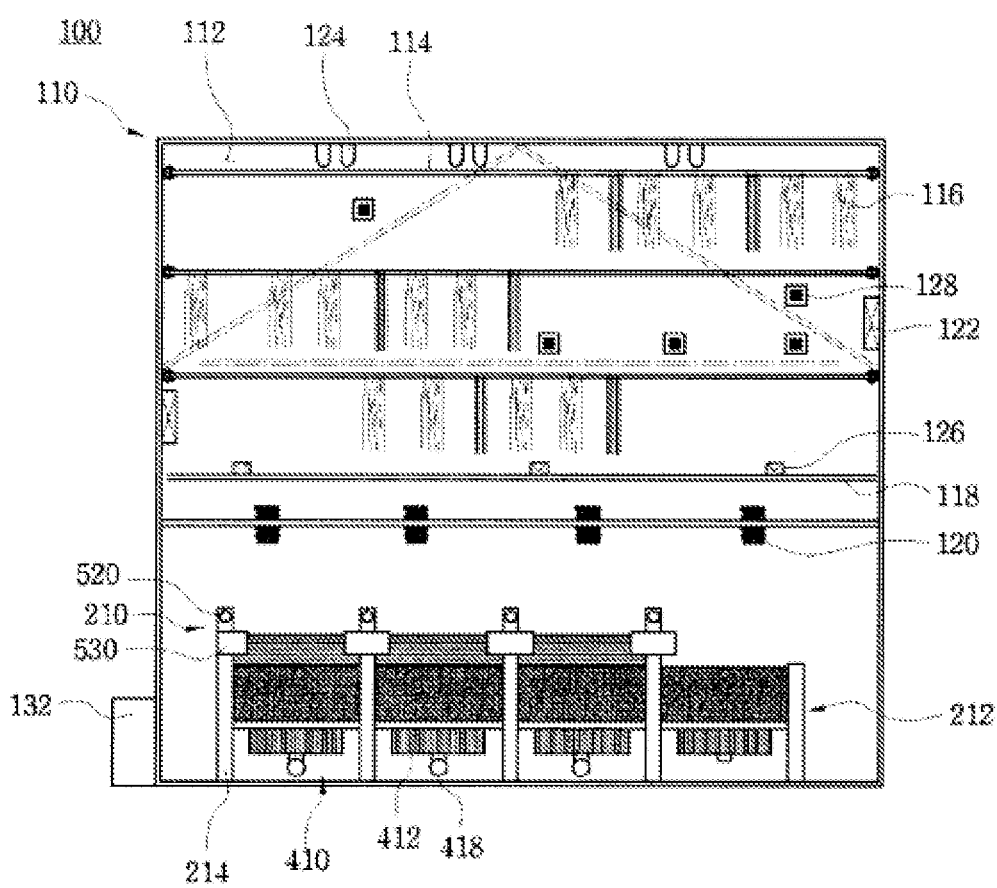
FIG. 1 is a cross partial view illustrating an apparatus for consecutively breeding fly larvae according to the present invention.
Figure 2:
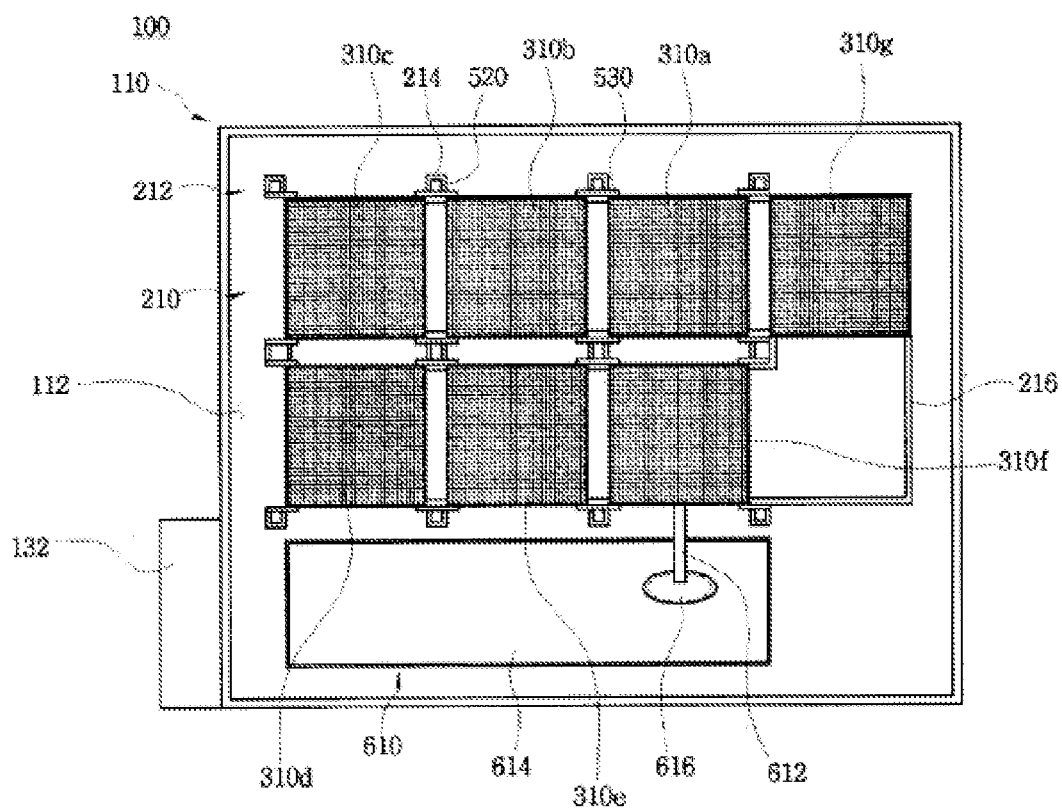
FIG. 2 is a plane view illustrating an apparatus for consecutively breeding fly larvae according to the present invention.
Figure 3A:
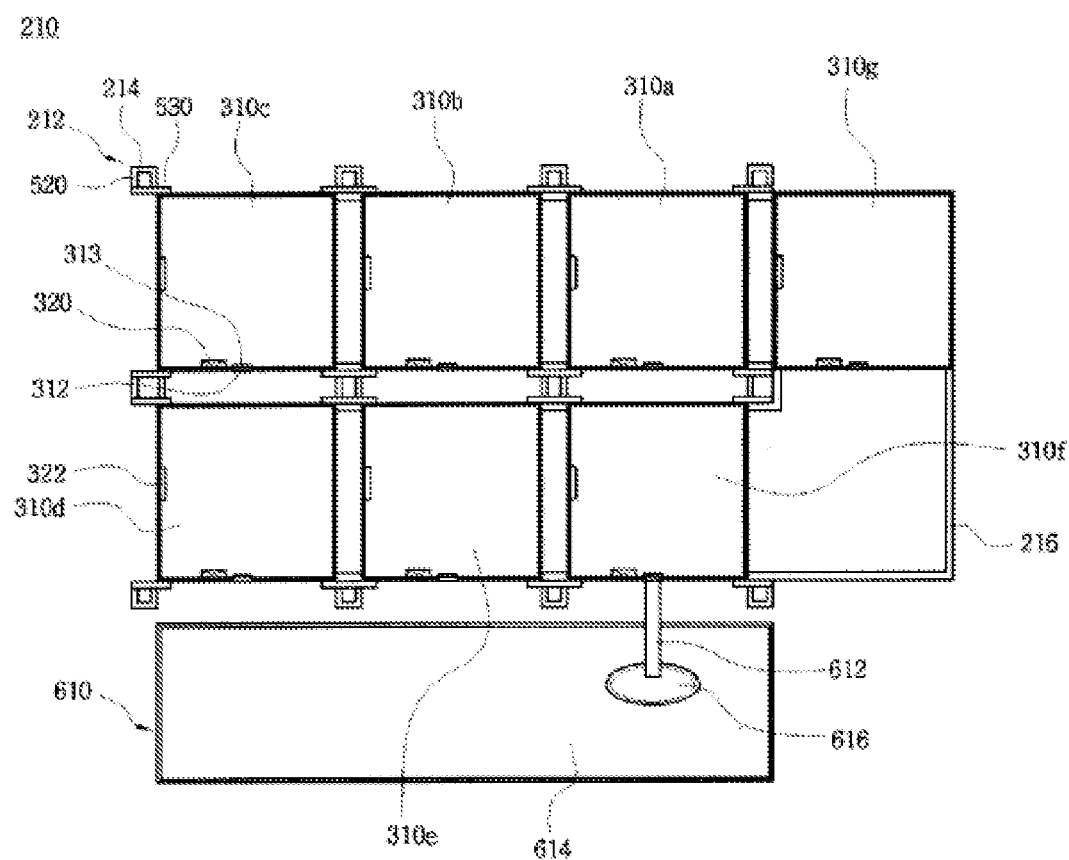
FIGS. 3A and 3B are views illustrating breeding chambers according to the present invention.
Figure 3B:
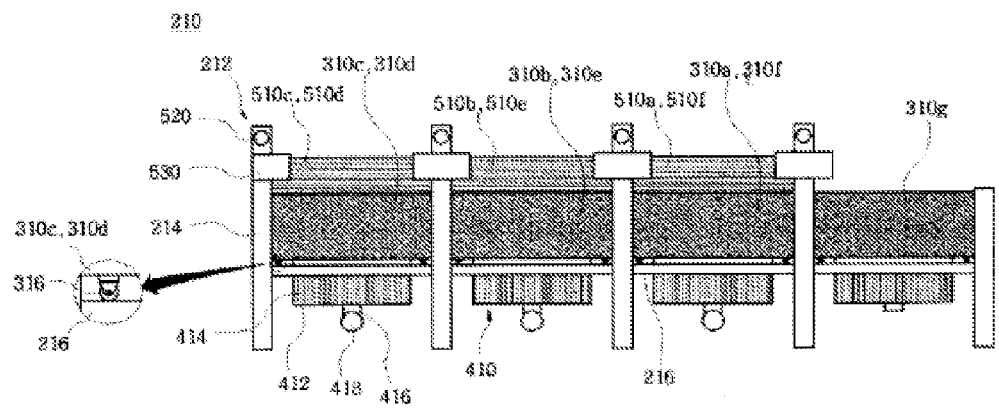
Figure 4:
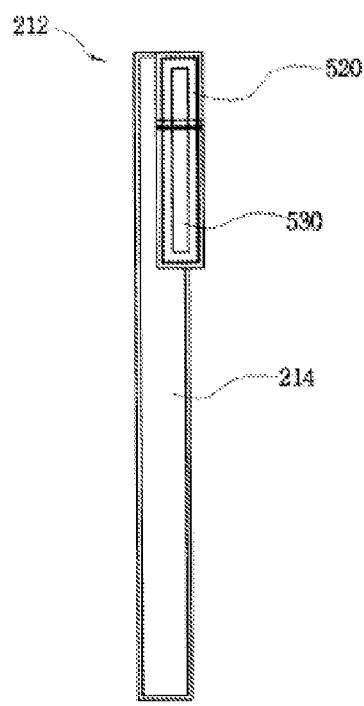
FIG. 4 is a view illustrating a pillar unit according to the present invention.
Figure 5:
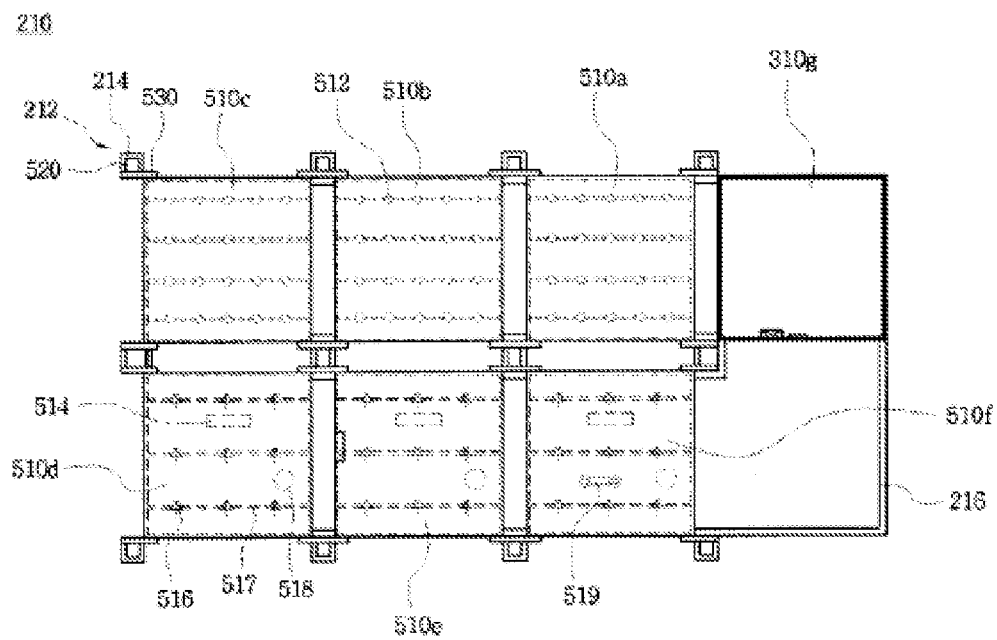
FIG. 5 is a view illustrating a cover according to the present invention.
Figure 6:
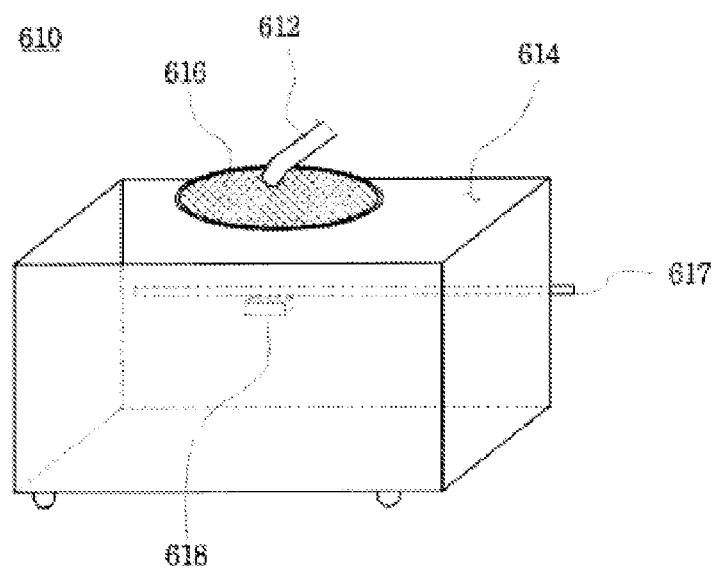
FIG. 6 is a view illustrating a metamorphosis chamber according to the present invention.

FIG. 1 is a cross partial view illustrating an apparatus for consecutively breeding fly larvae according to the present invention. FIG. 2 is a plane view illustrating an apparatus for consecutively breeding fly larvae according to the present invention. FIGS. 3A and 3B are views illustrating breeding chambers according to the present invention. FIG. 4 is a view illustrating a pillar unit according to the present invention. FIG. 5 is a view illustrating a cover according to the present invention. FIG. 6 is a view illustrating a metamorphosis chamber according to the present invention.

As illustrated in FIGS. 1 to 6, the apparatus for consecutively breeding fly larvae 100 according to the present invention may include a fly habitat part 110 which is sealed and includes a fly habitat chamber 112.

Here, the fly habitat part 110 includes a plurality of wires 114, a gore 116 on which flies may take rest, a first heating pipe 118 configured to keep an indoor temperature of the fly habitat chamber 112, a first ventilator 120, an air purifier 122, a lighting lamp 124, a first detection and measure sensor 126, a water supply facility 128, and a vacuum cleaner (not illustrated) configured to suck impurities from the floor and to treat them. The above-listed components are included in the Korean Patent Registration No. 10-104636 which was invented by the same applicant as the present application. The detailed descriptions thereon will be omitted.

On an outer side portion of the fly habitat part 110, there is provided a steam boiler 132 configured to supply steam to the first heating pipe 118.

In addition, in the fly habitat chamber 112 of the fly habitat part 110, there is installed a larvae breeding part 210 wherein flies may oviposit and larvae may be bred.

At this time, the larvae breeding part 210 includes a pillar unit 212 which is installed on the floor of the fly habitat chamber 112, and first to seventh breeding chambers 310a, 310b, 310c, 310d, 310e, 310f and 310g which are movable about the pillar unit 212 and are independently divided from one another.

The pillar unit 212 may include a plurality of pillar members 214 which are installed on the floor of the fly habitat chamber 112 of the fly habitat part 110.

The pillar member 214 are arranged in three rows in horizontal directions at regular intervals in their forward, backward, leftward and rightward directions, thus forming eight installation spaces in a quadrangle shape between the neighboring pillar members 214.

In the center of the plurality of the pillar members 214, a track-shaped rail 216 is installed as they are connected to one another. The first to seventh breeding chambers 310a, 310b, 310c, 310d, 310e, 310f and 310g are movable along the rail 216 for thereby forming a quadrangle closed-loop.

Therefore, since the pillar members 214 may be arranged in a rectangular shape, not in a circular shape, the first to seventh breeding chambers 310a, 310b, 310c, 310d, 310e, 310f and 310g may be installed for thereby producing as much larvae as possible using to the max the space of the fly habitat chamber 112 of the fly habitat part 110.

In addition, in a plurality of installation spaces formed between the pillar members 214, the first to seventh breeding chambers 310a, 310b, 310c, 310d, 310e, 310f and 310g are arranged in a quadrangle shape matching with the installation space formed in a quadrangle shape between the neighboring pillar members 214.

At this time, when the first to seventh breeding chambers 310a, 310b, 310c, 310d, 310e, 310f and 310g are installed in the eight installation chambers formed between the pillar members 214, any of the first to seventh breeding chambers 310a, 310b, 310c, 310d, 310e, 310f and 310g is not installed in a predetermined installation space while leaving it empty.

Therefore, the first to seventh breeding chambers 310a, 310b, 310c, 310d, 310e, 310f and 310g may be arranged in a quadrangle shape, thus utilizing to the max the spaces of the fly habitat chamber 112, which leads to increased production of larvae.

Here, the first to seventh breeding chambers 310a, 310b, 310c, 310d, 310e, 310f and 310g each are formed in quadrangle shapes wherein there are spaces whose tops are open. A passage 312 communicating with the spaces is formed at one side of each of the first to seventh breeding chambers 310a, 310b, 310c, 310d, 310e, 310f and 310g. There is provided an opening and closing door 313 which closes and opens the passage 312

In a corner of a lower side of each of the first to seventh breeding chambers 310a, 310b, 310c, 310d, 310e, 310f and 310g, there is provided a wheel 316 which is mounted on the rail 216 of the pillar unit 212 and by which the first to seventh breeding chambers 310a, 310b, 310c, 310d, 310e, 310f and 310g may move in one direction.

The moving means configured to move, by one room, the first to seventh breeding chambers 310a, 310b, 310c, 310d, 310e, 310f and 310g may be substituted from the wheel 316 disposed at the bottom of each of the first to seventh breeding chambers 310a, 310b, 310c, 310d, 310e, 310f and 310g to a sprocket, and the rail 216 installed in the pillar unit 214 may be substituted with a chain engaged to the sprocket for thereby moving the first to seventh breeding chambers 310a, 310b, 310c, 310d, 310e, 310f and 310g. Here, all types of moving means may be adapted so as to move the first to seventh breeding chambers 310a, 310b, 310c, 310d, 310e, 310f and 310g. The descriptions on the moving means configured to move the first to seventh breeding chambers 310a, 310b, 310c, 310d, 310e, 310f and 310g will be omitted.

The second ventilator 320 is installed in the first to seventh breeding chambers 310a, 310b, 310c, 310d, 310e, 310f and 310g. The second detection and measure sensor 322 may be installed so as to detect the temperature and humidity of the first to seventh breeding chambers 310a, 310b, 310c, 310d, 310e, 310f and 310g.

Below the first to seventh breeding chambers 310a, 310b, 310c, 310d, 310e, 310f and 310g, the suction discharge unit 410 is installed so as to suck and discharge impurities.

At this time, it is possible to obtain the same effects even when the second ventilator 320 and the second detection and measure sensor 322, which are installed in the first to seventh breeding chambers 310a, 310b, 310c, 310d, 310e, 310f and 310g, are installed in the first through sixth covers 510a, 510b, 510c, 510d, 510e and 510f.

The suction discharge unit 410 is installed below each of the first to seventh breeding chambers 310a, 310b, 310c, 310d, 310e, 310f and 310g, and there is further provided a discharge container 412 equipped with a filter 414. A discharge pipe 416 is provided below the discharge container 412. A vacuum pump 418 is installed at a predetermined portion of the discharge pipe 416.

In the pillar unit 212, there are provided the first through sixth covers 510a, 510b, 510c, 510d, 510e and 510f configured to cover tops of the first to seventh breeding chambers 310a, 310b, 310c, 310d, 310e, 310f and 310g.

The first through sixth covers 510a, 510b, 510c, 510d, 510e and 510f are installed matching with the first to seventh breeding chambers 310a, 310b, 310c, 310d, 310e, 310f and 310g. The top of any of the first to seventh breeding chambers 310a, 310b, 310c, 310d, 310e, 310f and 310g is open.

There is provided an ascending and descending member 520 configured to ascend or descend the first through sixth covers 510a, 510b, 510c, 510d, 510e and 510f. The ascending and descending member 520 is installed in the pillar member 214 so as to ascend or descend the first through sixth covers 510a, 510b, 510c, 510d, 510e and 510f.

At this time, the ascending and descending member 520 is installed in the pillar member 214, and all types of cylinder means may be used so as to ascend or descend the first through sixth covers 510a, 510b, 510c, 510d, 510e and 510f which are configured to cover tops of the first to seventh breeding chambers 310a, 310b, 310c, 310d, 310e, 310f and 310g. The detailed descriptions on the ascending and descending member 520 will be omitted.

When the first through sixth covers 510a, 510b, 510c, 510d, 510e and 510f disposed on tops of the first to seventh breeding chambers 310a, 310b, 310c, 310d, 310e, 310f and 310g descend and cover tops of the first to seventh breeding chambers 310a, 310b, 310c, 310d, 310e, 310f and 310g, a locking member 530 is provided so as to keep in safe the covering states on tops of them. The locking member 530 is installed in the pillar member 214

When the first to seventh breeding chambers 310a, 310b, 310c, 310d, 310e, 310f and 310g move to the next stage, the first through sixth covers 510a, 510b, 510c, 510d, 510e and 510f ascend. When the first through sixth covers 510a, 510b, 510c, 510d, 510e and 510f ascend, they are unlocked from the locking member 530 and ascend. After the first through sixth covers 510a, 510b, 510c, 510d, 510e and 510f complete ascending upward, the first to seventh breeding chambers 310a, 310b, 310c, 310d, 310e, 310f and 310g are unlocked from the locking member 530 and move along the rail 216, to the next stage. After the first to seventh breeding chambers 310a, 310b, 310c, 310d, 310e, 310f and 310g complete moving, the breeding chambers are secured by the locking member 530, and at the same time the first through sixth covers 510a, 510b, 510c, 510d, 510e and 510f descend and cover tops of the first to seventh breeding chambers 310a, 310b, 310c, 310d, 310e, 310f and 310g and are fixedly secured to the locking member 530.

Meanwhile, to the first through sixth covers 510a, 510b, 510c, 510d, 510e and 510f, a fog spray member 512, a feeder 514 and a stream boiler 132 may be connected depending on the growth conditions by growth stages of larvae. A water supply pipe 517 equipped with a shower 516 and a CCTV 518 may be installed.

More specifically, in the first to third covers 510a, 510b and 510c, the fog spray member 512 may be installed. In the fourth to sixth covers 510d, 510e and 510f, the feeder 514 and the shower 514 are installed. The water supply pipe 517 is connected to the steam boiler 132. The CCTV 518 is installed so as to observe the growths of larvae.

In the sixth cover 510f, the vacuum suction unit 518 is installed so as to collect the grownup larvae.

To the first through sixth covers 510a, 510b, 510c, 510d, 510e and 510f, the fog spray member 512, the feeder 514 and the stream boiler 132 may be connected depending on the growth conditions by growth stages of larvae. The descriptions on the construction and operations of the water supply pipe 517 equipped with the shower 516 and the CCTV 518 may be omitted because they are same as the construction and operations described in the Korean Patent Registration No. 10-104636 invented by the same applicant as the present application.

In the fly habitat chamber 112 of the fly habitat part 110, there is installed a metamorphosis chamber 610 wherein the larvae bred in the larvae breeding part 210 metamorphose.

The metamorphosis chamber 610 includes a connection passage 612 connected with the passage 312 formed in the sixth breeding chamber 310f which is positioned on the sixth day portion among the first to seventh breeding chambers 310a, 310b, 310c, 310d, 310e, 310f and 310g. The metamorphosis chamber 614 is provided in the other side of the connection passage 612 connected to the passage 312 of the sixth breeding chamber 310f.

At this time, lead mold, sawdust, sand and/or soil are mixed at a predetermined ratio and are inputted in the floor of the metamorphosis chamber 614 so as to make environment where the grownup larvae may metamorphose.

Between top of the metamorphosis chamber 614 and the exit of the connection passage 612, there is provided an electronic scale sensor 616 which is configured to control the opening and closing door 313 which opens or closes the passage 312 of the first to seventh breeding chambers 310a, 310b, 310c, 310d, 310e, 310f and 310g.

The second heating pipe 617 is installed so as to adjust the temperature of the metamorphosis chamber 614. The temperature detection sensor 618 is installed so as to detect a predetermined temperature.

Since the metamorphosis chamber 610 is the same as in the Korean Patent Registration No. 10-014636 invented by the same applicant as the present application, the detailed descriptions thereon will be omitted.

The operations of the apparatus for consecutively breeding larvae according to the present invention will be described.

Figure 7A:
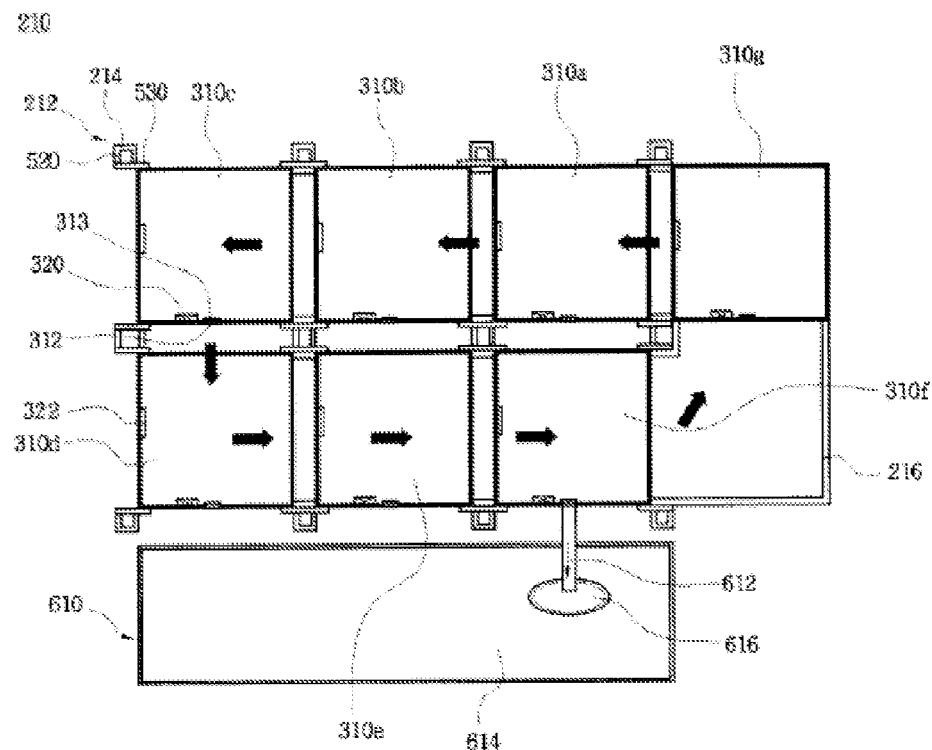
FIGS. 7A and 7B are views illustrating the operations of an apparatus for consecutively breeding fly larvae according to the present invention.
Figure 7B:
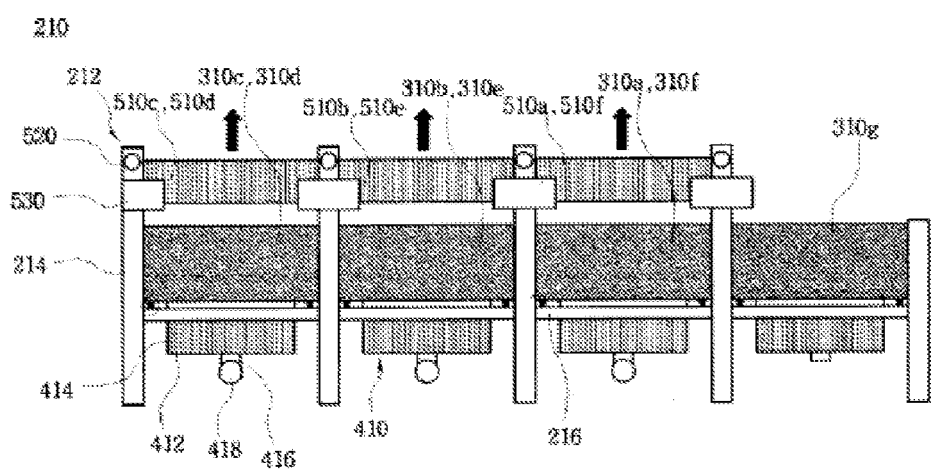

FIGS. 7A and 7B are views illustrating the operations of an apparatus for consecutively breeding fly larvae according to the present invention.

As illustrated therein, the apparatus for consecutively breeding larvae 100 according to the present invention is partly the same as in the Korean Patent Registration No. 10-104636 invented by the same applicant as the present application, so the descriptions on the same components will be omitted. Only the different operations will be described.

In the present invention, the separately arranged first to seventh breeding chambers 310a, 310b, 310c, 310d, 310e, 310f and 310g are arranged in quadrangle shapes, which leads to using the optimized space of the fly habitat camber 110 of the fly habitat part 110 and to producing as much larvae as possible.

The flies move from the fly habitat chamber 112 into any of the first to seventh breeding chambers 310a, 310b, 310c, 310d, 310e, 310f and 310g which is not covered by any of the first through sixth covers 510a, 510b, 510c, 510d, 510e and 510f among the first to seventh breeding chambers 310a, 310b, 310c, 310d, 310e of the larvae breeding part 210, more specifically, the flies move from the fly habitat chamber 112 into the seventh breeding chamber 310g whose top is not covered by the first through sixth covers 510a, 510b, 510c, 510d, 510e and 510f and oviposit.

Among the first to seventh breeding chambers 310a, 310b, 310c, 310d, 310e, 310f and 310g, the seventh breeding chamber 310a is called a chamber where the flies oviposit.

In a state where the flies oviposit in the seventh breeding chamber 310g of the larvae breeding part 21, the locking member 530 is unlocked after one day, and the first through sixth covers 510a, 510b, 510c, 510d, 510e and 510f ascend by the ascending and descending member 530, and the first to seventh breeding chambers 310a, 310b, 310c, 310d, 310e, 310f and 310g move along the rail 216, to the next stage by one room.

The seventh breeding chamber 310g where the flies have oviposited moves to the position of the neighboring first breeding chamber 310a, and the first breeding chamber 310a moves to the position of the second breeding chamber 310b. More specifically, the first to seventh breeding chambers 310a, 310b, 310c, 310d, 310e, 310f and 310g each move by one room per day in the above described manner, and the larvae grown in the sixth breeding chamber 310f are collected, and after the collection is finished, the sixth breeding chamber 310f moves to the position of the seventh breeding chamber 310g.

While the first to seventh breeding chambers 310a, 310b, 310c, 310d, 310e, 310f and 310g each move to the next stage per day, when the first to seventh breeding chambers 310a, 310b, 310c, 310d, 310e, 310f and 310g complete moving, the first through sixth covers 510a, 510b, 510c, 510d, 510e and 510f which have ascended or descend by means of the ascending and descending member and are locked by the locking member 530 and at the same time cover tops of the first to seventh breeding chambers 310a, 310b, 310c, 310d, 310e, 310f.

The locking member 530 is unlocked whenever one day passes, and the first through sixth covers 510a, 510b, 510c, 510d, 510e and 510f ascend, and at the same time the first to seventh breeding chambers 310a, 310b, 310c, 310d, 310e, 310f move by one room thus providing optimized habitat environment for each growth stage of larvae. The larvae are grown in the larvae breeding part 210 until sixth days when the larvae may be products.

At this time, the first through sixth covers 510a, 510b, 510c, 510d, 510e and 510f installed on tops of the first to seventh breeding chambers 310a, 310b, 310c, 310d, 310e, 310f may be set from the first day to the sixth day of larvae growth depending on the positions of the tops of the first to seventh breeding chambers 310a, 310b, 310c, 310d, 310e, 310f.

The method for making good growth environment so that the larvae may grow under comfort and sanitary environments by days in the first to seventh breeding chambers 310a, 310b, 310c, 310d, 310e, 310f using the devices installed in the first through sixth covers 510a, 510b, 510c, 510d, 510e and 510f is described in the Korean Patent Registration No. 10-104636, so the descriptions thereon will be omitted.

On the sixth day when the growth of larvae is completed, the opening and closing door 313 installed in the sixth breeding chamber 310f is opened for thereby opening the passage 312. The grownup larvae come out of the opened passage 312 and move through the connection passage 612, to the metamorphosis chamber 614 while heading for the light from the connection passage 612.

At this time, the larvae who move through the connection passage 612, to the metamorphosis chamber 614 passes through the electronic scale sensor 616 installed in the metamorphosis chamber 614.

While the larvae headed for the metamorphosis chamber 614 passes through the electronic scale sensor 616, when the larvae reach a predetermined weight level, the opening and closing door 313 is automatically closed based on the sensing of the electronic scale sensor 616, and the passage 312 is closed.

Part of the larvae bred in the sixth breeding chamber 310f moves through the passage 312, to the metamorphosis chamber 614 and metamorphose into flies, and the metamorphosed flies move into the habitat chamber 112 and inhabit therein and move into the seventh breeding chamber 310g and oviposit therein.

The flies oviposit, and the larvae grow until sixth day, and part of the larvae of the sixth day move into the metamorphosis chamber 614 and metamorphose into flies, and the metamorphosed flies inhibit in the fly habitat chamber 112 and move into the seventh breeding chamber 310g whose top is open and oviposit therein. The above-described process is repeatedly performed, thus consecutively producing larvae.

As a means for discharging outside the secretion or the excretion generating during the growth of larvae, the suction discharge unit 410 is same as in the Korean Patent Registration No. 10-104636 which is invented by the same applicant as the present application, so the detailed descriptions thereon will be omitted.

The first to seventh breeding chambers 310a, 310b, 310c, 310d, 310e, 310f and 310g are arranged in quadrangle shapes and are configured to move along the rail 216, thus utilizing to the max the space of the fly habitat chamber 112, which results in producing as much larvae as possible.

It is possible to prevent overload to the apparatus for consecutively breeding larvae 100 in such a way that the first through sixth covers 510a, 510b, 510c, 510d, 510e and 510f are configured to ascend or descend in place by means of the ascending and descending member 520, and only the first to seventh breeding chambers 310a, 310b, 310c, 310d, 310e, 310f and 310g are configured to move by room whenever alarm generates per day along the rail 216.

In a space in the floor of the sealed fly breeding chamber 112, the larvae breeding chamber 210 and the fly metamorphosis chamber 614 are installed for thereby providing the optimized habitat environment. The larvae with the exception of those having escaped to the metamorphosis chamber are collected, and the metamorphosed flies move into the fly habitat part 110 and oviposit therein, the ecological circulation cycles of which are repeatedly performed, thus consecutively producing good larvae.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

INDUSTRIAL APPLICABILITY

The present invention relates to an apparatus for consecutively breeding fly larvae, and in particular to an apparatus for consecutively breeding fly larvae which makes it possible to automatically breed larvae by repeatedly performing a process wherein in a state where a breeding chamber is divided into a plurality of breeding chambers configured to breed larvae in, the grownup larvae with the exception of those having escaped to a metamorphosis chamber are collected, and the larvae who escaped to the metamorphosis chamber are grown into flies, and the flies move to a habitat chamber installed above the breeding chambers and are bred and oviposit in the breeding chamber.

What is claimed is:
1. An apparatus for consecutively breeding fly larvae, comprising:
a fly habitat part;
a larvae breeding part which is installed in the fly habitat part; and
first through sixth covers which are configured to cover a top of the larvae breeding part, wherein the larvae breeding part includes
a pillar unit which is installed on a floor of the fly habitat part, and
first to seventh breeding chambers which are installed in the pillar unit and are configured to independently operate with respect to one another, and
wherein the pillar unit includes
a plurality of pillar members on which the first through sixth covers are installed,
an ascending and descending member installed on a top portion of each of the plurality of pillar members so as to ascend or descend the first through sixth covers, and a rail installed in a middle portion of the plurality of pillar members so as to guide the first to seventh breeding chambers.

2. The apparatus of claim 1, wherein said each of the plurality of pillar members comprises a locking member which is configured to fix the first through sixth covers.

3. The apparatus of claim 1, wherein the first to seventh breeding chambers are arranged in quadrangle shapes, each of the first to seventh breeding chambers being open in a top and having a space inside thereof, and a chamber passage is formed at one side of the first to seventh breeding chambers.

4. The apparatus of claim 3, wherein a wheel is installed in each corner of a lower side of each of the first to seventh breeding chambers and is mounted on the rail installed in the plurality of pillar member of the pillar unit.

5. The apparatus of claim 4, wherein a suction discharge unit configured to suck and discharge impurities is installed at lower sides of the first to seventh breeding chambers.

6. The apparatus of claim 5, wherein below the first to seventh breeding chambers, the suction discharge unit comprises a discharge container equipped with a filter inside,
a discharge pipe is installed at a lower side of the discharge container, and
a vacuum pump is installed in the discharge pipe.

7. The apparatus of claim 1, wherein the first through sixth covers are separately installed while matching with the first to seventh breeding chambers, and each of the first to seventh breeding chambers is open.

8. The apparatus of claim 1, wherein a metamorphosis chamber is installed in a fly habitat chamber of the fly habitat part and is configured to communicate with a chamber passage formed in the first to seventh breeding chambers of the larvae breeding part.

9. The apparatus of claim 8, wherein the metamorphosis chamber comprises a connection passage through which to communicate with the chamber passage of the first to seventh breeding chambers and an electronic scale sensor is installed at an end portion of the connection passage.

10. The apparatus of claim 1, wherein the first to seventh breeding chambers move along the rail and move in a quadrangle closed loop.

* * * * *